United States Patent [19]
Engerstam

[11] 3,940,989
[45] Mar. 2, 1976

[54] BRAKE POWER CONTROLLING DEVICE

[76] Inventor: Marten Engerstam, Kopmansvagen 42, Huddinge, Sweden, S-141 41

[22] Filed: Apr. 15, 1974

[21] Appl. No.: 460,721

[30] Foreign Application Priority Data
Apr. 19, 1973 Sweden............................. 7305593

[52] U.S. Cl. ................................................. 73/379
[51] Int. Cl.² ........................................... G01L 5/02
[58] Field of Search ....... 73/135, 379, 507; 188/180

[56] References Cited
UNITED STATES PATENTS

| | | | |
|---|---|---|---|
| 887,616 | 5/1908 | Field | 73/507 |
| 1,749,569 | 3/1930 | Florez | 73/507 X |
| 3,192,772 | 7/1965 | Tarter | 73/379 |
| 3,765,245 | 10/1973 | Hampl | 73/379 |
| 3,767,195 | 10/1973 | Dimick | 73/379 |
| 3,845,663 | 11/1974 | Blomberg et al. | 73/379 |

*Primary Examiner*—Charles A. Ruehl
*Attorney, Agent, or Firm*—Laff, Whitesel & Rockman

[57] ABSTRACT

A device for controlling the braking power in a brake equipment of a bicycle exerciser is capable of keeping the brake power of this equipment constant or giving it a programmed variation. The device comprises a non-electronic comparing means, which compares the existing power of the equipment (represented by a first r.p.m.), with the desired power of the equipment (represented by a second r.p.m.). If there is a difference between these two r.p.m., the comparing means delivers an output signal in the form of a third r.p.m., which signal is utilized to control a brake setting means for the brake equipment, such that the first and the second r.p.m. are brought into accordance.

18 Claims, 5 Drawing Figures

BRAKE POWER CONTROLLING DEVICE

This invention relates to a brake power controlling device used for load tests, for instance, for motors or preferably in brake equipments for appliances for physical training and/or for condition training, e.g. appliances in the form of bicycle exercisers and/or ergometers.

The present invention has for its object to control the brake equipment in any of these kinds of apparatuses in such a way that the power is maintained constant or so that it is given a programmed variation. Here an object is to obtain independently of the speed or number of revolutions of the energy source supplying the power to the brake equipment.

It is thus possible for an individual pedaling a bicycle exerciser, provided with the inventive control device, to deliver during the whole training period a constant, preselected power, independently of how he varies the pedal speed. If the pedal speed is increased, the control device will decrease the brake power of the brake equipment in such a way that the mechanical power will be the desired one. Inversely if the pedal speed is decreased the control device will increase the brake power, so that the magnitude of the mechanical power is maintained. It is possible to maintain the power constant or to vary this power according to a special program. For instance, the training may be of the type "oxygen uptake training" or of the type "lactic-acid training". Such variation can be achieved automatically through inserting in the control device the desired program in the form of a suitable program carrier, e.g. a cam.

Known devices maintain the mechanical power constant and/or for obtain a programmed variation of the mechanical power, independent of the rotational speed. These devices are used for brake equipments in bicycle exercisers, but they are all based on electrical or electronic control systems and are relatively expensive. The high price makes it impossible to sell them elsewhere than to certain research institutions and public institutions. Notwithstanding such price. They ought to be used in every case, where a programmed and well controlled training is necessary, as for instance for hard training sportsmen and for heart disease patients. Mechanical devices for maintaining a constant power of brake equipments have been designed. However the control effect of these devices has not been based on the difference between the existing and the desired powers, but, for instance, on an increase or a decrease of the speed or the revolution of the brake equipment as a control technical error signal, a method which means certain difficulties when the error signal are to be evaluated. Mechanical brake power control devices, which enable a programmed variation of the power, have not been known heretofore.

The basic idea of the invention is that a first r.p.m., which is proportional to or is in another way suitable is functionally related to the power absorbed at a certain moment by a brake equipment. This first r.p.m. is compared in a mechanical way with a second r.p.m., which is proportional to or is in another way suitably related to the desired power. At the actual moment when it is desired to have energy absorbed by the brake equipment, a third r.p.m. is caused by this comparison. The third r.p.m. is a distinct measure of the eventual difference between the first and the second r.p.m. Through a mechanical arrangement, the third r.p.m. accomplishes such an increase or a decrease of the brake power existing in the brake equipment that the existing and the desired powers are brought into accordance. The r.p.m., which corresponds to the desired power, can be maintained constant or be varied, e.g. automatically according to a prescribed program, and thus control the existing power in an intended manner. In order to prevent the brake power from being unfavourably large at low speeds or revolutions of the brake equipment, for instance when starting the apparatus or bringing it to a standstill, a special device can be provided, which at these occasions enables a limitation of the brake power.

Reference may be made to the following specification and accompanying drawings describing and showing preferred embodiments of the invention, wherein.

Figure 1:
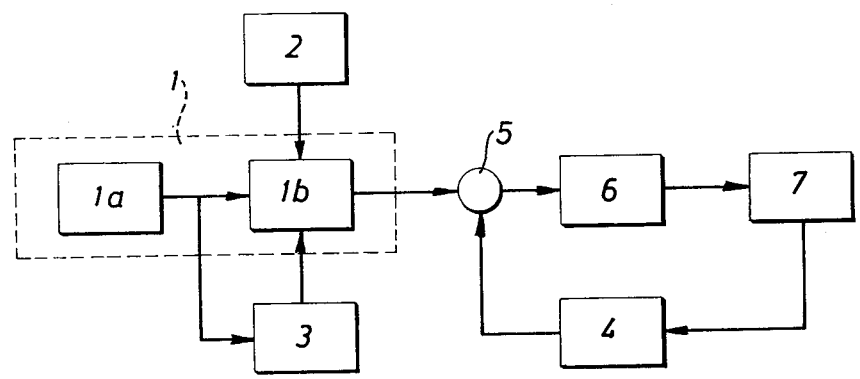
FIG. 1 is a block diagram of one embodiment of the control system.

In the embodiment of the control system, which is shown in the block diagram according to FIG. 1, the existing and the desired powers are each represented by an r.p.m. The r.p.m. which represents the desired power is obtained from an r.p.m. delivering device 1. This device comprises a rotating device 1a, e.g. a centrifugal governor or an electric motor, and a setting device 1b, which may be a variable gear transforming the output r.p.m. from the rotating device, this r.p.m. being presumed to be constant. Otherwise this setting device may consist of an adjusting member for actuating the r.p.m. of the rotating device. This adjusting member is for instance, a rheostat which may be used when the rotating device is an electric motor or a tensioning device for adjusting a spring counteracting upon a centrifugal force when the rotating device is a centrifugal governor. The control of the output r.p.m. from the r.p.m. delivering device 1 may be accomplished by means of either a manual actuation by an adjusting member 2 or an automatic regulation from a programstoring device 3. If this device uses cams or similar program carriers moved at constant speed, the operation may be achieved by a suitable connection of the program-storing device with the rotating device 1a, mentioned before, provided that this latter one is intended to rotate at constant speed.

The r.p.m. representing the existing power is obtained from a mechanical, analogue integrator 4, for instance of the Kelvin-type, for integrating the brake power existing in the brake equipment with the speed of a braked element of said equipment.

The r.p.m. representing the existing power and the r.p.m. representing the desired power are supplied to a mechanical comparing device, in the following called differential gear 5. This differential gear delivers to its output shaft an r.p.m. which is proportional to, or eventually is suitable in another form, and functional connection with, the difference between the existing and the desired powers. This proportional r.p.m. is fed to a mechanism 6, which controls the brake power applied to the braked element 7 of the brake equipment.

Figure 2:
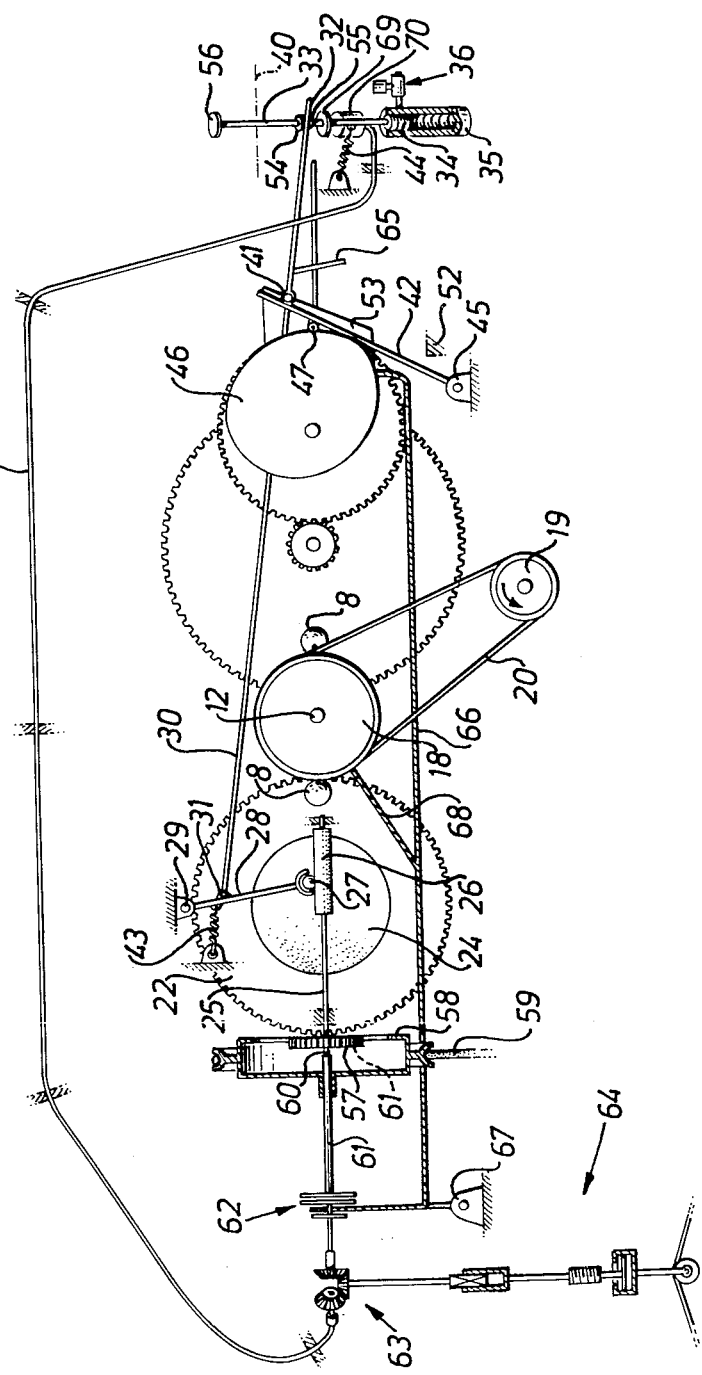
FIG. 2 is a side view of one embodiment according to the invention.
Figure 3:
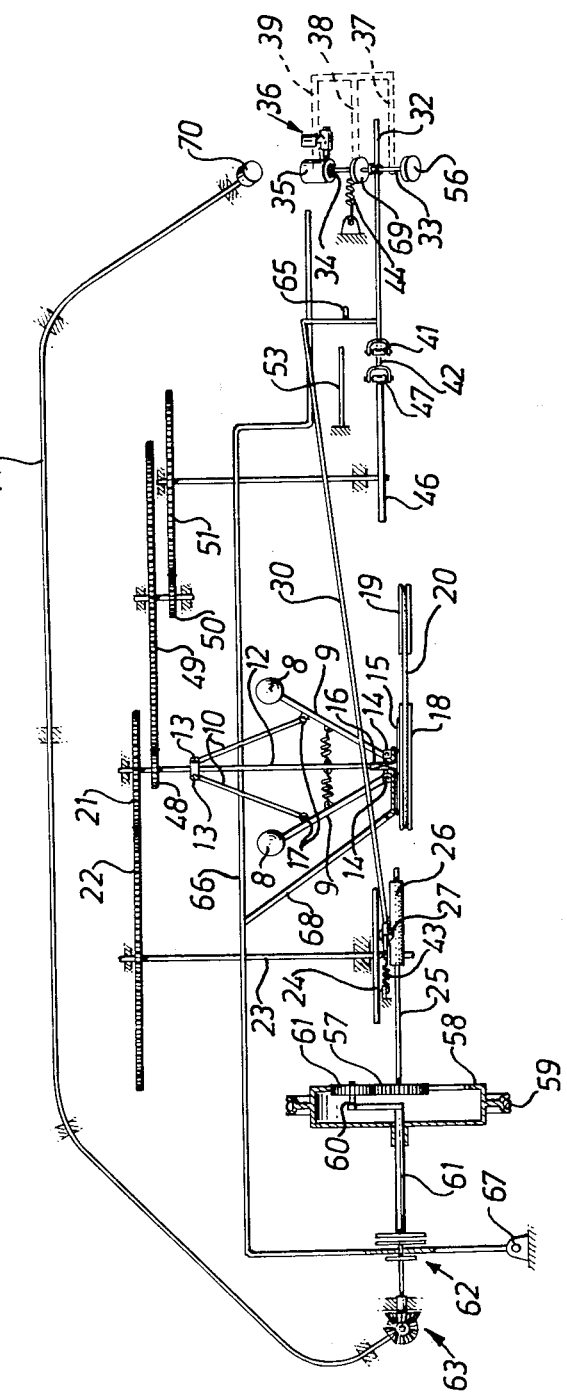
FIG. 3 is a plan view of the same embodiment.

In the embodiment of the invention which is shown in FIGS. 2 and 3 a constant r.p.m. is provided by means of a centrifugal governor haivng two pendulum arms 9, each with one fly weight 8, two link arms 10, one draw spring 11 and one shaft 12. The link arms 10 are each attached to the shaft 12 in a joint 13, so that they can be turned to form different angles with the shaft but cannot rotate about it. In the same way, the pendulum arms 9 are attached to the hub of a friction disc 15, each via a joint 14. This friction disc is mounted around a square formed portion 16 of the shaft 12 in such a way that it can be axially displaced along said shaft, but cannot rotate around it. The pendulum arms 9 are further connected to the link arms 10 by means of joints 17. Through a cooperation with the pendulum arms 9, the link arms 10, the shaft 12 and the joints 13, 14 and 17, the draw spring 11 tends to displace the friction disc 15 axially towards a pulley 18, which is rotating freely about the shaft 12, but is not axially displaceable. When rotating, the centrifugal force of the shaft 12 forces fly weights 8 away from this shaft and tend, through cooperation with the pendulum arms 9, the link arms 10, the shaft 12 and the joints 13, 14 and 17, to displace the friction disc 15 axially in the direction away from the pulley 18.

The pulley 18 is driven at a constant r.p.m. or a varying r.p.m., which is higher than the constant r.p.m., except when starting the apparatus or bringing it to a standstill. The constant r.p.m. is the speed wanted to take out from the shaft 12. If the control device is used in a bicycle exerciser, for example, the operation of the pulley 18 can be made by means of a belt 20 extending from a pulley 19 connected to the flywheel of the exerciser. When the pulley 18 begins to rotate, the friction disc 15 is pressed through the force of the spring 11 is pressed against this pulley 18, and the whole centrifugal governor is forced to rotate. The higher the rotational speed, the larger is the centrifugal force acting upon the fly weights 8 and the less effective is the engagement between the friction disc 15 and the pulley 16, which means that there will be a slipping action between these two elements enabling the centrifugal governor to maintain the desired r.p.m. as soon as this r.p.m. is exceeded by the pulley 18. If the r.p.m. of the centrifugal governor tends to be lowered below the desired value, the centrifugal force is decreased and thus the engagement between the friction disc 15 and the pulley 18 will be more effective, so that the slipping action between these two elements is decreased, and the r.p.m. of the centrifugal governor again reaches its intended value. If, on the other hand, the r.p.m. of the centrifugal governor tends to be too high, an increase of the slipping action is obtained in a similar way, which means that it will be a lowering of the r.p.m. to the desired, constant value.

The centrifugal governor is driven, via gear wheels 21 and 22, by an infinitely variable gear, consisting of an input shaft 23, a friction disc 24 fixedly connected thereto, an output shaft 25, a friction cylinder 26 fixedly connected thereto, a ball 27 being in contact with both the friction disc 24 and the friction cylinder 26, and further a lever 28. At its upper end, lever 28 is pivotedly mounted around a stationary point 29 such that is is turnable parallel to the plane of the friction disc 24. At its lower, lever 28 has a fork shaped end with a proper play which clasps the ball 27. This ball transfers to the friction cylinder 26 the tangential speed of the friction disc 24, which disc speed exists in the point where this disc is in contact with the ball 27. When the ball 27 is moved by means of the lever 28 parallel to the rotational symmetry axis of the friction cylinder 26, the r.p.m. ratio between the input shaft 23 and the output shaft 25 will be infinitely varied. Thereby these shafts 23 and 25, the friction disc 24, the friction cylinder 26, the ball 27 and the lever 28 constitute together an infinitely variable gear. This gear together with the centrifugal governor described above constitute the r.p.m. delivering device 1 in FIG. 1. The r.p.m. of the output shaft 25 according to FIGS. 2 and 3 has a magnitude representing the desired brake power.

The setting of the desired r.p.m. of the output shaft 25 is made by means of a pull rod 30, which in its one end is pivotedly mounted in a joint 31 on the lever 28, so that this lever can be brought to a proper angle position. The other end of the pull rod 30 is provided with a slot surrounds a control lever 33, 32 having closed ends, which slot with a suitable play in transverse direction. This control lever 33 is, at its lower end, provided with a thread 34 engaging the inside threads of a tube 35, which is supported by a double joint enabling the tilting of the control lever in two cross directions, so that it can be moved into and along each of three slots 37, 38 and 39 of a plate 40. When the control lever 33 is moved to the slot 37, which is the lowest one of the slots in FIG. 3, a roller 41 on the pull rod 30 is brought into engagement with a lever 42, as the pull rod 30 together with the lever 28 of the infinite variable gear is moved by a draw spring 43 to the left according to FIGS. 2 and 3. As also the control lever 33 is moved in the same direction by a draw spring 44. This lever cannot unfavourably affect the pull rod 30 through any contact with the right end of the slot 32 of this rod 30. The lever 42, which at its lower end is pivotedly mounted about a stationary shaft 45, is forced against the outer periphery of a cam 46 by means of the traction represented by the actuation of the spring 43 on the pull rod 30. The contact with the cam 46 takes place through mediation of a roller 47 pivotedly mounted on the lever 42. Through cooperation between the lever 42 and the pull rod 30, the cam 46 will regulate the angle position of the lever 28 of the infinite variable gear. Thus the r.p.m. of the output shaft 25 of this gear is also regulated. The cam is driven, via gear wheels 48, 49, 50 and 51, at a constant speed from the shaft 12 of the centrifugal governor and will therefore during its rotation continuously vary the r.p.m. of the infinite variable gear according to the program, which is materialized through the shape of the cam.

If it is desired to have the r.p.m. of the output shaft 25 of the infinite variable gear maintained constant and not varied in the time, the control lever 33 is moved to the middle slot 38. When the control lever 33 shall be moved from one slot to another, it must be moved so far to the right according to FIGS. 2 and 3 that it leaves the right end of the slot just occupied. When the control lever is in this right position it has, through engagement with the right end of the slot 32 of the pull rod 30, moved this rod to the right, so that its roller 41 is moved from engagement with and is free from the lever 42. By the gravity, the lever 42 has been tilted to the right and rests on a stationary support 52, thus leaving the contact with the cam 46, so that this can be replaced by another cam, if so is desired.

When the control lever 33 is moved from its right position and into the middle slot 38 as far as to the left limit position of this slot, the roller 41 of the pull rod 30, through the traction of the draw spring 43, will arrive into engagement with a stationary oblique stop member 53. The pull rod 30 is then kept in one and the same position, which means that also the lever 28 of the infinite variable gear will be maintained in one and the same position resulting in a constant r.p.m. of the output shaft of said gear. If it is so desired a lower, constant r.p.m. can be set by lowering the right end of the pull rod 30, so that the roller 41 is moved downwards along the oblique stop member 53, and due to the obliqueness of this member, is displaced to the left. This displacement to the left will, via the pull rod 30, actuate the lever 28 of the infinite variable gear, so that the ball 27 will be moved to a position nearer to the middle of the friction disc 24, the r.p.m. of the output shaft 25 being thereby lower. If, on the other hand, an increase of the r.p.m. of the output shaft 25 is desired, the right end of the pull rod must be raised. The lowering and the raise, respectively, of the right end of the pull rod 30 is achieved by means of the control lever 33, which for this purpose is provided with two disc shaped elements 54 and 55 located on each side of the slot 32 of the pull rod 30. Therefore, elements 54, 55 force the right end of the pull rod 30 to accompany the control lever, when it is moved downwards and upwards responsive to a rotation of the handle 56 of the control lever 33, which means that also this lever is rotated and screwed downwards and upwards in the threaded tube 35.

If the roller 41 of the pull rod 30 is in contact with the lever 42, following the contour of the cam 46, it is possible, by moving the right end of the pull rod upwards or downwards in the above described manner to move the roller 41 of the pull rod farther from or nearer to the shaft 45. This roller movement achieves a change of the r.p.m. of the output shaft of the infinite variable gear, which is caused by a certain change of the radius of the cam 46. The characteristics of this regulation of the r.p.m. variation is defined inter alia by the position of the shaft 45.

The r.p.m. representing the desired power and given to the output shaft 25 of the infinite variable gear is supplied to the sun wheel 57 of a planetary gear. To the outer wheel 58 of the same planetary gear is supplied, by means of a belt 59, the r.p.m. from a mechanical integrator (not shown). This r.p.m. represents the existing power and gives to the outer wheel 58 an inverse rotational direction in relation to that of the sun wheel 57.

When there is an accordance between the existing and the desired powers, the relationship between the r.p.m. of the sun wheel 57 and the outer wheel 58 is such that the planet carrier 60 of the planetary gear standstill. This carrier carries a planet wheel in engagement with the sun wheel 57 and the outer wheel 58. This means that the planet carrier shaft does not rotate. The output shaft 61 of the planetary gear serves the purpose of the differential gear 5 according to FIG. 1.

If the existing power is lower than the desired one, the r.p.m. of the outer wheel 58 will be lower than the value required for causing a standstill of the planet carrier 60. This means that the planet carrier rotates in the same direction as the sun wheel 57 and at an r.p.m. corresponding to how much the existing power is below the desired one. The rotation given to the output shaft 61 will operate, via a friction clutch 62 and a gear 63, a brake power setting device 64 corresponding to the control mechanism 6 according to FIG. 1. Brake setting is such a way that the brake power and thus the mechanical power is increased. If the existing power is higher than the desired one, the planet carrier 60 will rotate in the same direction as the outer wheel 58, i.e., in an opposite direction as compared with the preceding case. The brake power setting device 64 will thereby be affected to lower the brake power.

In order to prevent an unfavourably large brake power at slow speeds of the rotating element of the brake equipment, as when starting the apparatus or bringing it to a standstill, it is possible, to move the control lever as far as possible to the right. This movement is transferred to the pull rod 30 and the lever 28 of the infinite variable gear, to move the ball 27 outwards from the center of the friction disc 24. This operation prevents the r.p.m. of the output shaft 25 from being too low, which should cause too high desired power and thus high brake power.

If it is desired to disengage the automatic power control, the control lever 33 is moved into the upper slot 39 according to FIG. 3. The right end of the pull rod is thereby displaced laterally, so that a projection 65 on the pull rod will arrive into contact with the right part of a disengagement lever 66. This lever rotates about its stationary shaft 67. This rotation of the disengagement lever 66 causes a disengagement of the friction clutch 62 and therethrough of the connection between the output shaft 61 of the planetary gear and the gear 63, driving the brake power setting device 64. The disengagement lever 66 also, by means of a branch 68, disengages the friction disc 15 of the centrifugal governor from the pulley 18. The centrifugal governor thereby loses its driving force and comes to a standstill. When the control lever 33 is moved to the left end of the slot 39 according to FIG. 3, a friction disc 69 on the control lever 33 is brought into contact with a friction cylinder 70, which through a flexible shaft 71 is capable of driving the gear 63, which in turn operates the brake power setting device 64. When the control lever 33 is in the position described, it is possible, through rotating the handle 56 of this lever, to manually adjust the brake power.

Figure 4:
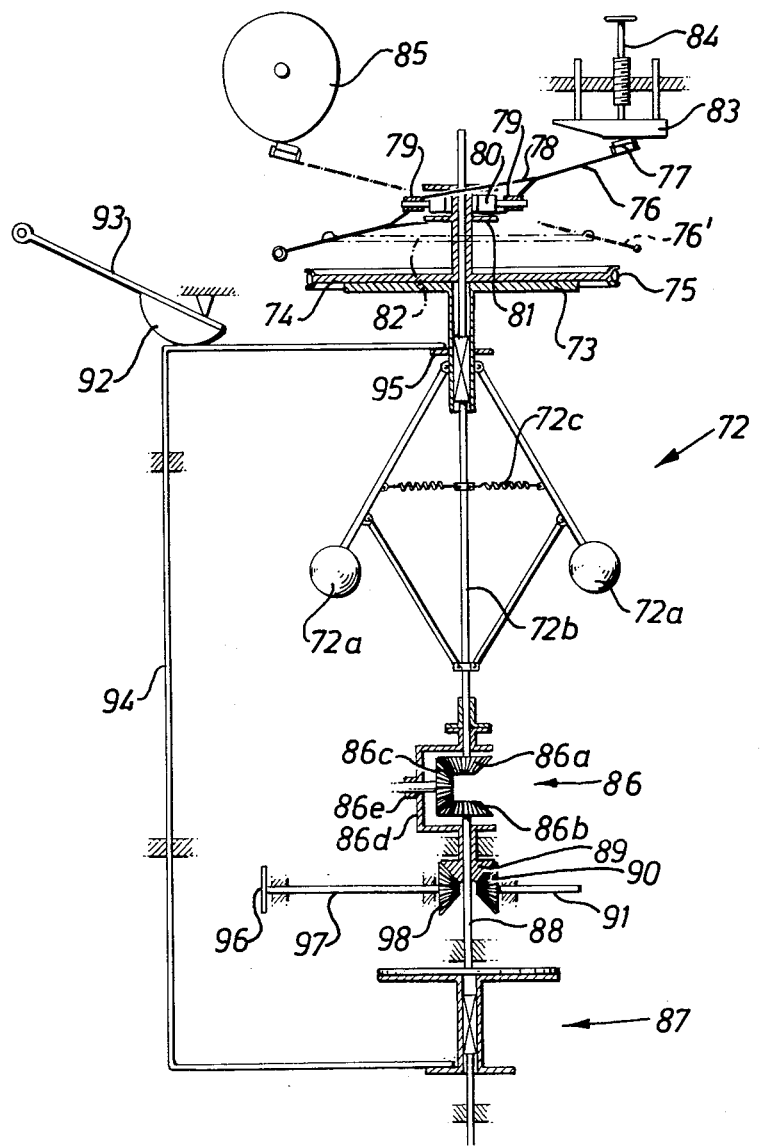
FIG. 4 is a plan view of another embodiment according to the invention.

In connection with FIG. 4, another more compact embodiment of the invention will now be described. This embodiment comprises a centrifugal governor 72, which is operated by a friction disc 73. Under a suitable degree of slipping, disc 73 is rotated by means of a pulley 74, which in turn is driven by a belt 75, receiving its driving force from, for instance, a rotating element in the brake equipment. The centrifugal governor 72 functions in the same way as is described in connection with the embodiment according to FIGS. 2 and 3, except that the driving system for the centrifugal governor has been modified suc that the output r.p.m. from said governor can be adjusted to the instantaneously desired value instead of, as in the preceding embodiment being preset once and for all. This modification is accomplished because the pulley 74, driving the centrifugal governor, is made axially displaceable. The nearer the pulley 74 is brought to the centrifugal governor 72, the farther the fly weights 72a of the governor must be forced out from the governor shaft 72b by means of the centrifugal force in counteraction to a force represented by a draw spring 72c. This means that the governor speed must be higher to start the slippage between the friction disc 73 and the pulley 74, and thereby the beginning of the constant speed of the governor.

The adjustment of the axial position of the pulley 74 and thus the control of the r.p.m. of the centrifugal governor is made by means of a lever 76. The upper end of this lever is provided with a roller 77. In the middle, the lever is branched to form a loop 78, which contains two bearings 79, in which a ring 80 is mounted. This ring engages a flange 81 of the pulley 74 and keeps this pulley in an axial position, which depends of the position of the lever 76. The lower end of the lever 76 passes through a slot 82 in a plate, which for the rest is not shown. When the lower end of the lever 76 is moved to the left end of the slot 82, the upper end of the lever 76 engages block 83 by means of the roller 77. A set screw 84 is displaceable in the axial direction thereof to control the position of lever 76. When the block 83 is vertically displaced, the lever 76 is rotated about a point, where the lever is engaging the one edge of the slot 82. The ring 80 engages the flange 81 and displaces the pulley 74 axially, the r.p.m. of the centrifugal governor is thereby changed. If the lever 76 is moved to the dashed-line position 76' and thereby located with its lower end in the right end of the slot 82, the position of the upper end of the lever will be controlled by a cam 85. Therefore, in analogy with what is described before, cam 85 controls the r.p.m. of the centrifugal governor 72. For each power program a special cam is required. The operation of the cam is achieved by means of a synchronous motor, a clock work or a centrifugal governor.

The comparison between the r.p.m. representing the desired power in the brake equipment and the r.p.m. representing its existing power is made by means of a differential gear 86. The desired r.p.m. is obtained from the centrifugal governor 72 and is supplied into the upper wheel 86a of the differential gear 86. The brake requirement r.p.m. is obtained from the integrator (not shown in FIG. 4) measuring the existing power in the brake equipment and corresponding to the integrator 4 according to FIG. 1. The integrator acts via a friction clutch 87 and a shaft 88 and is supplied into the lower wheel 86b of the differential gear 86. The rotational direction of the centrifugal governor 72 is so chosen, that the wheels 86a and 86b have opposite rotations in relation to each other. When the desired and the existing powers are the same, these wheels 86a and 86b are rotating at the same speed. This means that the intermediate wheel 86c of the differential gear will rotate, having its rotational symmetry axis in a fix direction. If the desired power is higher than the existing power, the intermediate wheel 86c will be forced by the upper wheel 86a to rotate about the axis of the latter. The r.p.m. of the wheel 86c, about this axis, depends on the difference between the r.p.m. of the upper wheel 86a and the lower wheel 86b. In the rotation of the intermediate wheel 86c about the axis of the upper wheel 86a, the housing 86d of the differential gear must also participate. This housing, through a bearing 86e, carries the intermediate wheel. The rotation of the housing 86d is transferred to a gear wheel 89, which through a gear wheel 90 and a shaft 91 is driving a brake power control device (not shown) such that the brake power of the brake equipment is increased. If the desired power is lower than the existing power, a process similar to that just described will take place, but resulting in such a rotational direction of the output shaft 91, that the brake power is decreased.

Disengagement of the brake power controlling device is accomplished in such a way that a lever 93 provided with a cam 92 is moved in such a direction that a U-shaped rod 94 is displaced. This rod moves a flange 95 axially and disengages the friction disc 73, driving the centrifugal governor, from the pulley. The rod 94 further disengages the friction clutch 87 connecting the governor with the power integrator of the brake equipment. When such a disengagement has been made, the desired brake power can be adjusted by means of a knob 96, which is connected through a shaft 97 and the three gear wheels 98, 89 and 90 to the shaft 91 driving the brake power controlling device.

For the two embodiments of the invention described above, the driving power to the control device is taken entirely or substantially from the rotating element of the brake equipment. If this power is not small in relation to the power braked by the brake equipment, it may be necessary to have the integrator (4 according to FIG. 1), which measures the existing power of the brake equipment, also to include the average driving power of the control device or, at higher requirements on accuracy, its instantaneous driving power. The latter procedure can be achieved by having a differential gear which measures how large the driving power is that is utilized by the control device at every moment and corrects the instantaneous value of the integrand in the above integrator in relation to the driving power. A device which can be used for this purpose is described in connection with FIG. 5.

Figure 5:
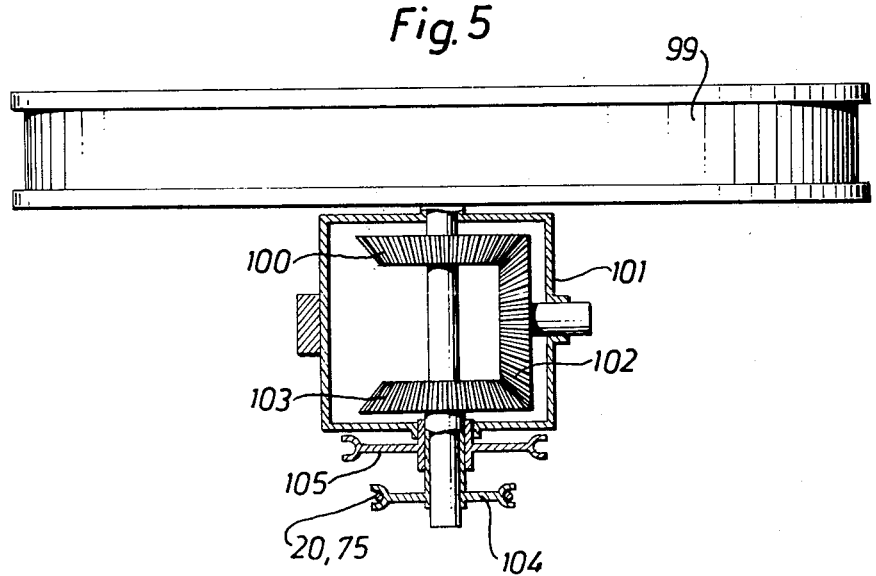
FIG. 5 is a plan view of a device to compensate for required driving power.

In the device according to FIG. 5, the rotating element 99 of the brake equipment is connected to a gear wheel 100 of a differential gear. In the housing 101 of this gear is pivotedly mounted an intermediate wheel 102, which is in engagement with this gear wheel 100 and with a third gear wheel 103 of the differential gear. This latter gear wheel is provided with a pulley 104 driving a belt 20 (according to FIGS. 2 and 3) or a belt 75 (according to FIG. 4), which in turn drives the power control device. The housing 101 of the differential gear is rotatable about the same geometrical axis as are the two opposite gear wheels 100 and 103 and is provided with a pulley 105, from which the rotation of the housing can be taken. When the power control device is driven, the pulley 104 for this drive and also the gear wheel 103 connected thereto are loaded by the required moment of driving. The intermediate wheel 102 is actuated by a periphery power at the location of the engagement with this wheel 103. In order to bring about an equilibrium of moments around the rotational symmetry axis of the intermediate wheel, the periphery power acting on the intermediate wheel at the location of engagement with the remaining gear wheel 100 must have the same direction and magnitude as the periphery power mentioned before. The result will be a moment acting on the housing 101 and thus on its pulley 105, which moment is twice the moment of driving acting on the other pulley 104. The moment on the pulley 105 of the housing 101 is applied through a suitable device transformed such that is can be added directly to the brake power (or the moment of braking) acting on the rotating element of the brake equipment. Thereafter, this sum is used to indicate the magnitude of the integrand of the power integrator.

When necessary the power control device can be provided with especial devices to indicate, for instance optically, a certain power or change of power.

The invention has here been shown and described in connection with some special embodiments. Of course these and other devices described here above can be modified in several ways within the scope of the invention.

What I claim is:

1. Brake equipment for controlling a braking power applied to a power source, said brake equipment having brake power setting means comprising means for selectively maintaining either a constant braking power or a programmed variable braking power for said brake equipment, non-electronic means for comparing two r.p.m., first means for producing a first one of said r.p.m. with a definite and functional relationship with the power from said source actually existing in said brake equipment, and second means for producing the second of said r.p.m. with a definite and functional relationship with the desired power of said brake equipment, said comparing means comprising means for delivering an output signal in the form of a third r.p.m. constituting a distinct measurement of the difference between said first and said second r.p.m., and means responsive to the output signal from said comparing means for controlling said brake power setting means to adjust the braking power of said brake equipment such that the desired and the existing powers are brought into accordance.

2. The brake equipment as claimed in claim 1, wherein said non-electronic means is a mechanical device.

3. The brake equipment as claimed in claim 2, wherein said non-electronic means is a mechanical gear.

4. The brake equipment as claimed in claim 1, wherein said second means comprises an adjustable centrifugal governor means.

5. The brake equipment as claimed in claim 4, wherein said second means comprises an infinitely variable speed output means operated responsive to the centrifugal governor.

6. The brake equipment as claimed in claim 5 wherein said second means further comprises means for driving said centrifugal governor responsive to the movement of a rotating element of said power source.

7. The brake equipment as claimed in claim 6, wherein said first means includes integrator means responsive to an average of the instantaneous driving power from said power source, which is also applied to said centrifugal governor, and said comparing means includes means responsive to said integrator means for adjusting the braking power and therefore the magnitude of a driving moment of the power source.

8. The brake equipment as claimed in claim 1 wherein said second means includes an automatic adjusting means including a programming cam for controlling said second r.p.m.

9. The brake equipment as claimed in claim 8, wherein the second means includes means responsive to the position of said cam for increasing or decreasing the second r.p.m.

10. The brake equipment as claimed in claim 9, wherein the means responsive to said cam position includes a lever having means for taking out a variable rotational speed as said second r.p.m.

11. The brake equipment as claimed in claim 8, and wherein said second means comprises means for positioning said cam responsive to the output of a power source which delivers a non-variable r.p.m.

12. The brake equipment as claimed in claim 1 wherein said second means comprises a cam operated at a rotational speed controlled by a centrifugal governor.

13. The brake equipment as claimed in claim 1 and means to disengage the second means, and means for manually adjusting the braking power of said brake equipment after said disengagement.

14. The brake equipment as claimed in claim 13 and means whereby all manual adjustment of the brake equipment and all manual adjustment of the braking power of said brake equipment are made by means of a single adjusting member.

15. The brake equipment as claimed in claim 1 and means for preventing an unfavourably large braking power when starting the power source or bringing it to a standstill, said last named means comprising a device which causes the second r.p.m. to be maintained within a preselected value range corresponding to a low desired power.

16. The brake equipment of claim 1 and means whereby an electrical motor having an adjustable r.p.m. provides said second r.p.m.

17. The brake equipment of claim 1 and means whereby a spring driven motor having an adjustable r.p.m. provides said second r.p.m.

18. The brake equipment of claim 1 and manual means for controlling said second r.p.m.

* * * * *